United States Patent [19]

Chen

[11] Patent Number: 6,096,346
[45] Date of Patent: Aug. 1, 2000

[54] METHOD OF OBTAINING EXTRACT OF SHARK'S CARTILAGE

[76] Inventor: Chun-Yuan Chen, No. 3, Lane 213, Sec. 5, Young-Ping N. Rd., Taipei City, Taiwan

[21] Appl. No.: 09/311,695

[22] Filed: May 13, 1999

[51] Int. Cl.[7] .................................................... A61K 35/60

[52] U.S. Cl. ........................... 424/548; 426/655; 426/437; 426/486; 435/273

[58] Field of Search ................................. 426/7, 539, 641, 426/655, 425, 437, 486, 488; 424/520, 523, 548; 435/273

*Primary Examiner*—Keith Hendricks
*Attorney, Agent, or Firm*—Rosenberg, Klein & Lee

[57] ABSTRACT

A method of obtaining an extract of shark's cartilage is provided wherein a shark's cartilage is processed through five steps. The five steps are smashing, cleaning, purifying, deodorizing, and sterilizing. The result of this process is a pure white product with no fishy smell.

6 Claims, 1 Drawing Sheet

METHOD OF OBTAINING EXTRACT OF SHARK'S CARTILAGE

BACKGROUND OF THE INVENTION

1. Field of the Invention

The invention is related to a method of obtaining an extract of shark's cartilage, especially a healthy way to obtain an extract of shark's cartilage without getting a fishy smell and where the color is pure white.

2. Prior Art

The result of a conventional way of obtaining the extract of shark's cartilage does not remove the fishy smell, and the conventional way does not have a "clean up" step. Conventionally, the marrow is ground or smashed into powder. This will make the product smell fishy, and the color will be gray or black. When consumers purchase or use these kinds of products, they do not feel comfortable taking them.

SUMMARY OF INVENTION

However, the main purpose of this invention is to resolve the above-mentioned problems, and provide another solution of obtaining this extract. The method steps are smashing, cleaning, purifying, getting rid of the smell, and sterilizing. The resulting product will be pure white with no fishy smell.

DETAILED DESCRIPTION OF PREFERRED EMBODIMENTS

Figure 1:
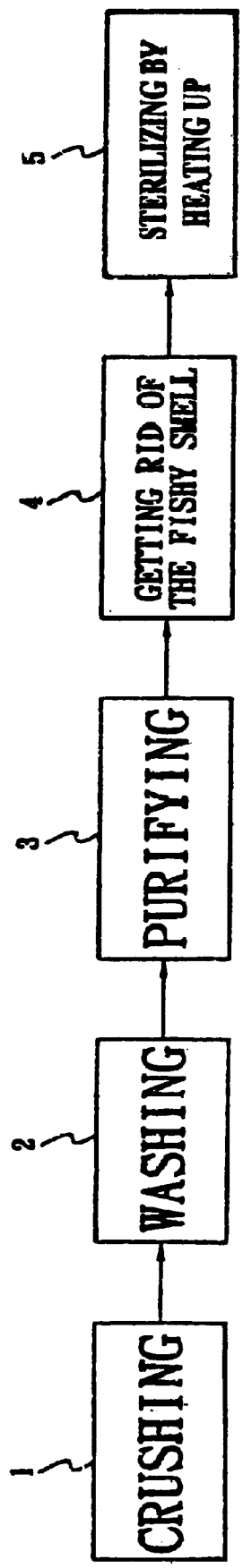
FIG. 1 is a block diagram of the process of the present invention.

With reference to FIG. 1, the method of extracting sharks' cartilage is described as follows:

The shark's cartilage is smashed by a crusher (1), the pressure is maintained at 3 kg/cm2±0.5 kg. After smashing the cartilage, the cartilage is washed (2). There are two methods of washing (2) the cartilage. The first one is to electrolyze the phosphate calcium out, and the other method is to wash the crushed cartilage with acid. Then, the phosphate calcium is separated by its difference in specific gravity and bleaching is carried out three times to purify (3). Next, enzymes are used to get rid of the fishy smell (4). Any kind of enzyme can be used. A test was conducted by using enzymes from apples. Sterilizing the cartilage under a vacuum at 131° C.±5° C., using steam at 70 PSI ±5 PSI (5) for 25 to 30 minutes. The results of these processes will produce a pure extract of shark's cartilage without a fishy smell.

What is claimed is:

1. A method of making an extract of shark's cartilage, comprising the steps of:

(a) smashing cartilage of a shark with a crusher;
   (b) removing a phosphate calcium composition from said smashed cartilage;
   (c) separating said phosphate calcium composition from said smashed cartilage using differences in specific gravity therebetween;
   (d) purifying said smashed cartilage by bleaching said smashed cartilage;
   (e) deodorizing said smashed cartilage using enzymes; and,
   (f) sterilizing said deodorized smashed cartilage under a vacuum at a predetermined temperature.

2. The method as recited in claim 1 where the step of smashing includes the step of maintaining a pressure of said crusher at 3 kg/cm$^2$±0.5 kg.

3. The method as recited in claim 1 where the step of removing includes a process selected from electrolyzing and acid washing.

4. The method as recited in claim 1 where the step of purifying includes bleaching said smashed cartilage three times.

5. The method as recited in claim 1 where said enzymes of step (e) are apple enzymes.

6. The method as recited in claim 1 where said predetermined temperature of step (f) is 131° C.±5° C.

* * * * *